(12) United States Patent
Shalaby et al.

(10) Patent No.: US 8,299,205 B2
(45) Date of Patent: *Oct. 30, 2012

(54) ACETONE-SOLUBLE, ABSORBABLE, CRYSTALLINE POLYAXIAL COPOLYMERS AND APPLICATIONS THEREOF

(75) Inventors: Shalaby W. Shalaby, Anderson, SC (US); James M Lindsey, Anderson, SC (US); Christof Merckle, Mannheim (DE); Helmut Goldmann, Tuttlingen (DE)

(73) Assignee: Poly-Med, Inc., Anderson, SC (US)

( * ) Notice: Subject to any disclaimer, the term of this patent is extended or adjusted under 35 U.S.C. 154(b) by 415 days.

This patent is subject to a terminal disclaimer.

(21) Appl. No.: 11/598,427

(22) Filed: Nov. 13, 2006

(65) Prior Publication Data

US 2007/0077382 A1  Apr. 5, 2007

Related U.S. Application Data

(60) Continuation-in-part of application No. 11/390,403, filed on Mar. 27, 2006, now Pat. No. 7,416,559, which is a continuation-in-part of application No. 10/630,320, filed on Jul. 30, 2003, now Pat. No. 7,070,858, which is a division of application No. 10/003,640, filed on Nov. 2, 2001, now abandoned, which is a continuation-in-part of application No. 09/698,527, filed on Oct. 27, 2000, now Pat. No. 6,462,169.

(51) Int. Cl.
*C08G 63/08* (2006.01)

(52) U.S. Cl. .......................... 528/354; 525/386; 525/415

(58) Field of Classification Search .................. 428/402, 428/36.9; 523/118; 528/54, 55, 81, 83, 905; 528/354; 525/386, 415
See application file for complete search history.

(56) References Cited

U.S. PATENT DOCUMENTS

| | | | |
|---|---|---|---|
| 4,429,080 A | 1/1984 | Casey | |
| 4,470,416 A | 9/1984 | Kafrawy | |
| 4,532,928 A | 8/1985 | Bezwada | |
| 4,543,952 A | 10/1985 | Shalaby | |
| 4,804,691 A * | 2/1989 | English et al. | 523/118 |
| 5,133,739 A | 7/1992 | Bezwada | |
| 5,403,347 A | 4/1995 | Roby | |
| 5,431,679 A | 7/1995 | Bennett | |
| 5,468,253 A | 11/1995 | Bezwada | |
| 5,554,170 A | 9/1996 | Roby | |
| 5,620,461 A | 4/1997 | Muijs Van de Moer | |
| 5,644,002 A | 7/1997 | Cooper | |
| 5,713,920 A | 2/1998 | Bezwada | |
| 5,951,997 A | 9/1999 | Bezwada | |
| 6,190,773 B1 * | 2/2001 | Imamura et al. | 428/402 |
| 6,206,908 B1 | 3/2001 | Roby | |
| 6,462,169 B1 | 10/2002 | Shalaby | |
| 6,794,485 B2 | 9/2004 | Shalaby | |
| 6,797,485 B2 | 9/2004 | Cassels | |
| 7,070,858 B2 | 7/2006 | Shalaby | |
| 7,129,319 B2 | 10/2006 | Shalaby | |
| 7,348,364 B2 * | 3/2008 | Shalaby | 514/772.1 |
| 2005/0143817 A1 * | 6/2005 | Hunter et al. | 623/11.11 |

FOREIGN PATENT DOCUMENTS

| | | |
|---|---|---|
| DE | 10 2006 053 752.1 | 11/2006 |
| EP | 0 618 250 A1 | 10/1994 |
| EP | 0 697 427 A2 | 2/1996 |
| EP | 0 712 880 A2 | 5/1996 |
| EP | 0 737 703 A2 | 10/1996 |

OTHER PUBLICATIONS

Correa et al., Sixth World Biomaterials Congress, Trans So.c Biomat., II, 992 (2000).
L. Mandelkern, Crystallization of Polymers, McGraw-Hill Book Company, NY, 1964, p. 105-106.
S.W. Shalaby, Chapter 3 of Thermal Characterization of Polymeric Materials (E.A. Turi ed.) Academic Press, NY, 1981, p. 330.
S.W. Shalaby and H.E. Blair, Chapter 4 of Thermal Characterization of Polymeric Materials (E.A. Turi ed.) Academic Press, NY, 1981, p. 402.

* cited by examiner

*Primary Examiner* — Gregory Listvoyb
(74) *Attorney, Agent, or Firm* — McCormick, Paulding & Huber LLP

(57) ABSTRACT

High-purity, acetone-soluble, absorbable components of medical devices are designed for optimum interfacing with human blood or the cell lining of a body cavity, and are formed of a crystalline, segmented l-lactide polyaxial copolymer structurally tailored to have certain molecular dimensions, thermal and physicomechanical properties, and solubility characteristics to allow their uses, optimally, as parts of vascular, urological, and post-surgical adhesion prevention devices.

9 Claims, No Drawings

ACETONE-SOLUBLE, ABSORBABLE, CRYSTALLINE POLYAXIAL COPOLYMERS AND APPLICATIONS THEREOF

CROSS-REFERENCE TO RELATED APPLICATIONS

This application is a continuation-in-part of U.S. Ser. No. 11/390,403, filed Mar. 27, 2006 now U.S. Pat. No. 7,416,559, which is a continuation-in-part of U.S. Ser. No. 10/630,320, filed Jul. 30, 2003, issued as U.S. Pat. No. 7,070,858, which is a division of U.S. Ser. No. 10/003,640, filed on 11/02/01 now abandoned, which is a continuation-in-part of U.S. Ser. No. 09/698,527, filed on Oct. 27, 2000 issued as U.S. Pat. No. 6,462,169.

FIELD OF THE INVENTION

This invention is directed toward a structurally tailored, acetone-soluble group of the absorbable polyaxial family of segmented copolyesters to meet specific requirements for their useful application as preferred alternatives to components of certain medical and surgical devices disclosed in the prior art. Specific applications include device components which interface with human blood and the cell lining of body cavities, such as endourological stents, endovascular stents, synthetic vascular grafts, scaffolds for tissue engineered blood vessels, and barriers for preventing post-surgical adhesion.

BACKGROUND OF THE INVENTION

Since the commencement of their development over four decades ago for use as surgical sutures, the family of absorbable polyesters has commanded a significant role as useful or potentially useful biomaterials for use in many medical and pharmaceutical applications. However, the existing and consistently growing applications of absorbable polyesters have been limited to a small number of polymers comprising linear chains, which (1) are usually melt-processable; (2) have limited solubility in common organic solvents; (3) are difficult to produce with a high degree of purity or in monomer-free forms, which can be critical to their successful use in certain biomedical applications; and (4) are practically unsuitable for producing high-compliance, resilient microfibers or films while retaining a minimum degree of crystallinity required for achieving dimensional stability and surface hardness. To address most of these shortcomings of linear polyesters, while reaching a new milestone in the design of absorbable polymers with exceptionally high degrees of freedom for molecular chain tailoring to meet unique requirements of contemporary medical devices in new as well as unfulfilled applications, the present inventor has introduced and implemented the concept of crystalline segmented, polyaxial copolyester chains comprising a monocentric, amorphous, highly compliant polyaxial core, end-grafted with crystallizable segments (U.S. Pat. Nos: 6,462,169; 6,794,485; 7,070,858; and 7,129,319). Success associated with the exceptional properties of this family of polyaxial segmented copolyesters provided a strong incentive to address further the linear polyester shortcomings, including those associated with polymer purity and solubility and to pursue the study subject of the present invention pertaining to precisely crafted polymer properties toward reaching a second milestone in the medical application of absorbable polyesters.

SUMMARY OF THE INVENTION

Thus, the present invention is directed to new, device-specific compositions of polyaxial copolyesters, which can be produced in highly purified form through precipitation/fractionation of their solutions in acetone. Specifically, this invention deals with high-purity, absorbable components of medical and surgical devices for use in contact with blood or cell linings of body cavities, wherein the components are formed of a crystalline, l-lactide acetone-soluble, polyaxial copolyester having a uniquely balanced set of properties entailing certain molecular dimensions, crystallinity, thermal properties, and physicomechanical properties tailored to meet their optimum use in tissue engineered blood vessels, endovascular stent mantles, endourological stents, barriers for post-surgical adhesion prevention, and synthetic vascular graft sealants.

This invention is generally directed toward an acetone-soluble, absorbable component of a medical device interfacing with human blood or the cell lining of a body cavity which is formed of a crystalline, segmented, l-lactide polyaxial copolyester made by end-grafting a monocentric polyaxial polymeric initiator with a certain mixture of cyclic monomers to form crystallizable terminal segments, thus producing a composition having a minimum solubility of 2 percent weight/volume in acetone, an inherent viscosity in chloroform of more than about 1.0 dL/g, melting temperature of more than about 100° C., a heat of fusion not exceeding about 20 J/g, a shore-A hardness of less than about 100, and an ultimate elongation in a film form exceeding about 100 percent, wherein the absorbable component is a leak-proof sealant for a synthetic vascular graft. More specifically, the synthetic vascular graft is a textile fabric of multifilament polyethylene terephthalate or a microporous, expanded polytetrafluoroethylene.

A specific aspect of this invention deals with an acetone-soluble, absorbable component of a medical device interfacing with human blood or the cell lining of a body cavity formed from a crystalline, segmented, l-lactide polyaxial copolyester made by end-grafting a monocentric polyaxial polymeric initiator with a certain mixture of cyclic monomers to form crystallizable terminal segments, thus producing a composition having a minimum solubility of 2 percent weight/volume in acetone, an inherent viscosity in chloroform of more than about 1.0 dL/g, melting temperature of more than about 100° C., a heat of fusion not exceeding about 20 J/g, a shore-A hardness of less than about 100, and an ultimate elongation in a film form exceeding about 100 percent, wherein the absorbable component is an electrospun, microfibrous mantle and the device is a metallic endovascular stent.

Another specific aspect of this invention deals with an acetone-soluble, absorbable component of a medical device interfacing with human blood or the cell lining of a body cavity formed of a crystalline, segmented, l-lactide polyaxial copolyester made by end-grafting a monocentric polyaxial polymeric initiator with a certain mixture of cyclic monomers to form crystallizable terminal segments, thus producing a composition having a minimum solubility of 2 percent weight/volume in acetone, an inherent viscosity in chloroform of more than about 1.0 dL/g, melting temperature of more than about 100° C., a heat of fusion not exceeding about 20 J/g, a shore-A hardness of less than about 100, and an ultimate elongation in a film form exceeding about 100 percent, wherein the absorbable component is a fiber-reinforced film and the device is a composite endoureteral stent.

A key aspect of this invention deals with an acetone-soluble, absorbable component of a medical device interfacing with human blood or the cell lining of a body cavity formed of a crystalline, segmented, l-lactide polyaxial copolyester made by end-grafting a monocentric polyaxial polymeric initiator with a certain mixture of cyclic monomers to form crystallizable terminal segments, thus producing a composition having a minimum solubility of 2 percent weight/volume in acetone, an inherent viscosity in chloroform of more than about 1.0 dL/g, melting temperature of more than about 100° C., a heat of fusion not exceeding about 20 J/g, a shore-A hardness of less than about 100, and an ultimate elongation in a film form exceeding about 100 percent, wherein the absorbable component is an electrospun microfibrous fabric and device is a scaffold for blood vessel tissue engineering. In addition, the absorbable component is an electrospun microfibrous, non-woven fabric and the device is a protective barrier for preventing post-surgical adhesion formation.

An important aspect of this invention deals with an acetone-soluble, absorbable component of a medical device interfacing with human blood or the cell lining of a body cavity formed of a crystalline, segmented, l-lactide polyaxial copolyester made by end-grafting a monocentric polyaxial polymeric initiator with a certain mixture of cyclic monomers to form crystallizable terminal segments, thus producing a composition having a minimum solubility percent weight/volume in acetone, an inherent viscosity in chloroform of more than about 1.0 dL/g, melting temperature of more than about 100° C., a heat of fusion not exceeding about 20 J/g, a shore-A hardness of less than about 100, and an ultimate elongation in a film form exceeding about 100 percent, wherein the absorbable component includes at least one bioactive agent selected from the group of antimicrobial agents, anti-inflammatory drugs, anti-thrombogenic agents, and tissue growth promoters.

DETAILED DESCRIPTION OF PREFERRED EMBODIMENTS

It has been acknowledged by many investigators that improperly selected blood-contacting polymeric materials, and particularly those comprising absorbable polymers, can inflict substantial damage to blood components, which in turn lead to a number of clinical complications. Among the key material-related root causes of these complications are the low mechanical compliance associated with high-modulus implants and the presence of cytotoxic leachables, such as residual monomers, which can be present in absorbable polymeric implants. Similarly, low-compliance polymeric implants and cytotoxic leachables can be detrimental to sensitive cell lining characteristics of body cavities, such as the blood vessel endothelial lining, cell lining of the peritoneal cavity, and cell lining of the urological tract. This created an obvious need to pursue the study subject of this invention dealing with the tailored synthesis of high-purity, essentially monomer-free, absorbable polymers, which can be easily fabricated into useful, absorbable components of vascular and urological devices, tissue engineering scaffolds, and barriers for post-surgical adhesion prevention without exposing the polymers to thermal treatments that may lead to thermally induced formation of cytotoxic leachables, as can be the case during the melt-processing of absorbable polyesters made by ring-opening polymerization. And, one objective of the present invention is to use tailor-made absorbable polymers, which are soluble in acetone, as a safe solvent, and hence, can be purified by dissolution in such solvent followed by precipitation into cold 2-propanol. This purification scheme does not only remove residual monomers, but also removes oligomeric impurities and a substantial fraction of the residual organometallic catalyst traditionally used in ring-opening polymerization. Removal of the oligomeric and organometallic impurities from absorbable polymers through the rigorous purification scheme described above is equally important to the removal of residual monomers relevant to undesirable effects on blood and cell linings. A further advantage of having absorbable polyesters, which form solutions in acetone at a wide range of concentrations, allows the athermal conversion of these polymers into adherent barrier films and solvents by simple solution casting or the formation of microfibers by electrostatic solution spinning.

To produce polyesters suited for such athermal processing, which, in turn, are converted to articles that are pure and compliant, requires unique designs of the polymeric chains. One of the key objectives of this invention is the extrapolation of the unique concept of having polyaxial polyester chains with a monocentric, amorphous core, having a glass transition temperature below 37° C., covalently bonded to crystallizable terminal segments, toward a new level of articulation to meet the specific requirements of optimally designed surfaces for safe interfacing with human blood and cell linings of selected body cavities. Subsequently, to meet this objective, certain thermal and physicomechanical properties, as well as macromolecular dimensions, were to be accomplished through the judicial design of the macromolecular chains, subject of the present invention.

Discussed below are examples of the uses of the polyesters subject of this invention, in most clinically useful and relevant applications of great significance to contemporary medical/surgical practitioners. The commanding role of drug-eluting, metallic stents in preventing restenosis following angioplasty can be further increased through the use of an electrospun, microfibrous cover (or mantle) made of at least one of the polymer(s) subject of the present invention. Advantages of the electrospun, drug-containing, electrospun microfibrous cover over non-absorbable polymeric coatings of commercially available drug-eluting stents have been addressed by this inventor in copending U.S. patent application (Ser. No. 11/390,403). Pressing needs for an absorbable endourological stent have been also addressed by this inventor in a copending U.S. patent application (Ser. No. 11/346,117), wherein an absorbable film was described as a key part of a composite construct. At least one of the copolyesters, subject of this invention, is well suited for use as a material for such film. Other applications of the polymers, subject of this invention, include their use as (1) electrospun microfibrous thin barrier sheets with and without a pharmaceutical adjuvant to prevent post-surgical adhesion formation associated with abdominal or ovarian surgeries; (2) an electrospun microfibrous scaffolding component of a tissue-engineered blood vessel; and (3) a leak-proof barrier sealant/film for a vascular graft made of polyethylene terephthalate multifilament constructs or microporous expanded polytetrafluoroethylene.

Further illustrations of the present invention are provided by the following examples:

EXAMPLE 1

General Method of Synthesis of Crystalline, Segmented Polyaxial, Copolyester Using Amorphous, Monocentric, Polyaxial Polymeric Initiators The amorphous polyaxial initiators, denoted as Segment I, were separately end-grafted with selected mixtures of cyclic monomers to form crystallizable terminal segments, II.

To prepare a polymeric initiator, Segment I, monomeric precursors, pre-dried triethanolamine, and tin(II) 2-ethyl hexanoate were added to a stainless steel reactor equipped for mechanical stirring and vacuum. The contents were dried at 40° C. under vacuum for 1 hour and the pressure equilibrated with dry nitrogen. The contents were stirred to ensure complete mixing and the temperature was raised to 180° C. The reaction was allowed to continue at 180° C. until 50-100% monomer conversion was achieved (as determined by gel permeation chromatography, GPC). The polymeric initiator was then either cooled to and maintained at room temperature for approximately 15 hours or maintained at 180° C. until the next step. The polymeric initiator was then heated (or cooled) to 110° C. and the monomeric components of Segment II were added. The mixture was stirred until the polymeric initiator was dissolved and then the temperature was raised to 160° C. (For polymers with a total monomer/catalyst molar ratio of 28,000, another equal aliquot of tin(II) 2-ethyl hexanoate was added prior to raising the temperature to 160° C.). The contents were stirred for about 30 minutes after the temperature reached 160° C. The stirring was then stopped and the Segment II reaction was continued by heating at 130-150° C. until essentially complete conversion was attained (as determined by GPC).

Upon completion of the polymerization, the polymer was removed and broken into ~1 in$^3$ pieces. Residual monomer was removed by distillation under reduced pressure at temperatures up to 80° C. The polymer was then further purified by precipitating its 20% (w/v) dichloromethane (DCM) solution using 2 parts −60° C. IPA in a commercial blender. The purified polymer was then dried to a constant weight under reduced pressure at temperatures up to 80° C. Additional purification was achieved by precipitating the purified polymer from a concentrated acetone solution into cold 2-propanol and isolated as a dry product as discussed above.

EXAMPLE 2

Synthesis of Representative Polyaxial Copolyester Compositions Using the General Method of Example 1

Using the general method of Example 1, nine representative polyaxial copolyesters were prepared as outlined in Table I. The polymers were isolated and purified as described in Example 1.

EXAMPLE 3

Characterization of Purified Representative Polyaxial Copolyester Compositions

Seven purified representative compositions of polyaxial copolyesters were characterized for their (1) molecular weight in terms of inherent viscosity in chloroform; (2) thermal properties (using differential scanning calorimetry) in terms of melting temperature ($T_m$); (3) heat of fusion ($\Delta H$) as a measure of crystallinity; and (4) degree of hardness in terms of shore-A hardness using room-temperature annealed molded wafers and a Durometer with the Shore-A scale. The analytical and testing data are summarized in Table II.

TABLE II

Properties of Purified Representative Polyaxial Copolyester Compositions

| Polymer Name | Shore Hardness[a] | I.V. (dL/g) | Thermal Data | |
|---|---|---|---|---|
| | | | $T_m$ (° C.) | $\Delta H$ (J/g) |
| Co-6 | 93.7 | 1.47 | 148 | 14.2 |
| Co-10 | 82.8 | 1.45 | 121 | 7.9 |
| Co-11 | 87.5 | 1.49 | 149 | 15.8 |
| Co-12 | 74.0 | 1.45 | 109 | 7.4 |
| Co-13 | 72.0 | 1.23 | 101 | 5.1 |
| Co-14A | 70.8 | 1.15 | 106 | 2.1 |
| Co-14B | 84.3 | 1.35 | 123 | 6.3 |
| Co-15 | 88.0 | 1.54 | 150 | 13.8 |

[a]Determined on room temperature annealed molded wafers (d = 12.7 mm, t = 1.8 mm) using a Durometer with the Shore hardness scale A.

Although the present invention has been described in connection with the preferred embodiments, it is to be understood that modifications and variations may be utilized without departing from the principles and scope of the invention, as those skilled in the art will readily understand. Accordingly, such modifications may be practised within the scope of the following claims. Moreover, Applicants hereby disclose all subranges of all ranges disclosed herein. These subranges are also useful in carrying out the present invention.

What is claimed is:

1. An acetone-soluble, absorbable polymer as a component of a medical device capable of beneficially interfacing with human blood and with the cell lining of a body cavity, the polymer comprising a film-forming, electrostatically spinnable, crystalline, segmented, 1-lactide polyaxial copolyester

TABLE I

Polymerization Schemes for the Synthesis of Representative Polyaxial Copolyester Compositions

| Polymer Name | Composition | | | Segment I Reaction Time at 180° C. (hr) | Segment II Reaction Time (hr)/ Temp (° C.) | Total Monomer/ Catalyst (molar) | Total Monomer/ Initiator (molar) |
|---|---|---|---|---|---|---|---|
| | Segment I CL/TMC/G (molar) | Segment II LL/CL/G (molar) | Overall CL/TMC/LL/G (molar) | | | | |
| Co-6 | 26/26/4 | 40/4/0 | 30/26/40/4 | 2 | 30/140 | 22,000 | 900 |
| Co-8 | 22/26/8 | 36/2/6 | 24/26/36/14 | 1 | 44/140 | 28,000 | 800 |
| Co-10 | 32/16/8 | 36/2/6 | 34/16/36/14 | 10 | 50/140 | 28,000 | 800 |
| Co-11 | 32/16/8 | 42/0/2 | 32/16/42/10 | 10 | 50/140 | 28,000 | 800 |
| Co-12 | 35/14/9 | 34/0/8 | 35/14/34/17 | 10 | 50/140 | 28,000 | 800 |
| Co-13 | 35/14/11 | 32/0/8 | 35/14/32/19 | 10 | 50/140 | 28,000 | 800 |
| Co-14A | 35/14/10 | 33/0/8 | 35/14/33/18 | 10 | 25/150–25/140 | 28,000 | 800 |
| Co-14B | 35/14/10 | 33/0/8 | 35/14/33/18 | 10 | 50/130 | 28,000 | 800 |
| Co-15 | 35/13/8 | 42/0/2 | 35/13/42/10 | 10 | 50/140 | 28,000 | 800 | made by end-grafting a monocentric polyaxial polymeric initiator with a mixture of cyclic monomers, thereby covalently bonding crystallizable terminal segments onto an amorphous core, the amorphous core having a glass transition temperature below 37° C., the copolyester having a minimum solubility of 2 percent weight/volume in acetone, an inherent viscosity in chloroform of more than about 1.0 dL/g, a melting temperature of more than about 100° C., a heat of fusion of up to about 20 J/g, a shore-A hardness of less than about 100, and an ultimate elongation of greater than about 100 percent in film form.

2. An acetone-soluble, absorbable polymer as set forth in claim 1 in the form of a leak-proof sealant for a synthetic vascular graft.

3. An acetone-soluble, absorbable polymer as set forth in claim 2 wherein the synthetic vascular graft comprises a textile fabric of multifilament polyethylene terephthalate.

4. An acetone-soluble, absorbable polymer as set forth in claim 2 wherein the synthetic vascular graft comprises a microporous, expanded polytetrafluoroethylene.

5. An acetone-soluble, absorbable polymer as set forth in claim 1 in the form of an electrospun, microfibrous mantle for a metallic endovascular stent.

6. An acetone-soluble, absorbable polymer as set forth in claim 1 in the form of a fiber-reinforced film for a composite endoureteral stent.

7. An acetone-soluble, absorbable polymer as set forth in claim 1 in the form of an electrospun microfibrous fabric for use in a scaffold for blood vessel tissue engineering.

8. An acetone-soluble, absorbable polymer as set forth in claim 1 in the form of an electrospun microfibrous, nonwoven fabric for use as a part of a protective barrier for preventing post-surgical adhesion formation.

9. An acetone-soluble, absorbable polymer as set forth in claim 1 further comprising at least one bioactive agent selected from the group consisting of antimicrobial agents, anti-inflammatory drugs, anti-thrombogenic agents, and tissue growth promoters.

* * * * *